(12) United States Patent
Ericson et al.

(10) Patent No.: US 9,149,343 B2
(45) Date of Patent: Oct. 6, 2015

(54) DENTAL INSTRUMENT, SYSTEM AND METHOD

(75) Inventors: Dan Ericson, Upplands Vasby (SE); Jan Johansson, Upplands Vasby (SE); Orjan Arkang, Upplands Vasby (SE); Stefan Leffler, Upplands Vasby (SE); Olof Larsson, Uppland Vasby (SE)

(73) Assignee: Directa AB, Upplands Vasby (SE)

( * ) Notice: Subject to any disclaimer, the term of this patent is extended or adjusted under 35 U.S.C. 154(b) by 75 days.

(21) Appl. No.: 13/143,654

(22) PCT Filed: Jan. 20, 2010

(86) PCT No.: PCT/SE2010/050048
§ 371 (c)(1),
(2), (4) Date: Aug. 31, 2011

(87) PCT Pub. No.: WO2010/087758
PCT Pub. Date: Aug. 5, 2010

(65) Prior Publication Data
US 2011/0306007 A1    Dec. 15, 2011

(30) Foreign Application Priority Data
Jan. 27, 2009   (SE) ...................................... 0900081

(51) Int. Cl.
  *A61C 7/00*   (2006.01)
  *A61C 5/12*   (2006.01)
(52) U.S. Cl.
  CPC ................. *A61C 5/127* (2013.01); *A61C 5/125* (2013.01)
(58) Field of Classification Search
  CPC .................................. A61C 5/125; A61C 5/127
  USPC ............ 433/148–149, 39–41, 226, 215–216; 132/321–329
  See application file for complete search history.

(56) References Cited

U.S. PATENT DOCUMENTS

| | | | |
|---|---|---|---|
| 3,772,790 A | 11/1973 | Swan-Gett et al. | |
| 3,795,052 A * | 3/1974 | Mowery | 433/39 |
| 3,815,243 A | 6/1974 | Eames | |
| 5,730,592 A * | 3/1998 | Meyer | 433/39 |
| 6,468,080 B1 | 10/2002 | Fischer et al. | |
| 2003/0113688 A1* | 6/2003 | Weissenfluh | 433/149 |
| 2004/0248064 A1 | 12/2004 | Rodriguez del Val | |

(Continued)

FOREIGN PATENT DOCUMENTS

| | | |
|---|---|---|
| DE | 3816501 A1 | 11/1989 |
| DE | 19936461 A1 | 2/2001 |
| WO | 2006056989 A1 | 6/2006 |

OTHER PUBLICATIONS

Supplementary European Search Report for corresponding European Patent Application No. 10736097.6, mailed Jul. 3, 2015.

*Primary Examiner* — Heidi M Eide
(74) *Attorney, Agent, or Firm* — Holland & Hart LLP

(57) ABSTRACT

A dental instrument, suitable for use when creating a dental filling, is provided. The dental instrument includes a wedge and a matrix. The matrix is fixedly attached to the wedge, and the wedge is adapted to be inserted into the approximal space between two teeth of a patient. The wedge has a bow shape along a length axis of the wedge, the matrix has a first bow shape along a length axis of the matrix, and the matrix also has a second bow shape along an axis perpendicular to the length axis of the matrix. A method of using the dental instrument and a disposable system, which further comprises a protective member, is further provided.

6 Claims, 4 Drawing Sheets

(56) References Cited

U.S. PATENT DOCUMENTS

| | | |
|---|---|---|
| 2005/0089813 A1 | 4/2005 | Slone |
| 2005/0089814 A1 | 4/2005 | Slone |
| 2005/0255428 A1 * | 11/2005 | Coopersmith ............. 433/222.1 |
| 2007/0087310 A1 | 4/2007 | Giusti |
| 2008/0241787 A1 | 10/2008 | Hegedus |

\* cited by examiner

DENTAL INSTRUMENT, SYSTEM AND METHOD

FIELD OF INVENTION

The present invention relates generally to a dental instrument, a disposable dental system and a method of using said dental instrument and disposable dental system.

BACKGROUND

Dental caries, also described as "tooth decay" or "dental cavities", is an infectious disease which damages the structures of the teeth. Dental caries can lead to pain and tooth infection. Dental caries often starts on the surfaces between adjacent teeth, also known as the approximal space. Proximal caries is one of the most common forms of caries.

The most common treatment of dental caries comprises the steps of excavating the tooth for removing the decayed part, this is usually done with a dental drill, whereafter a curing filling material is placed in the cavity to restore the function, integrity and morphology of the missing tooth structure.

When restoring a tooth it is of importance that the tooth returns to its original position in contact with the adjacent tooth and that the filling does not create what is called an overhang in the approximal space. An overhang is created if the dentist fails to seal off the preparation box, thus enabling the filling material to flow into the approximal space. The excess material creates an edge underneath the filling in which food remains can be trapped which usually leads to new dental caries or gingivitis.

Dental instruments have been used to close off a hole or trench made for the purpose of receiving a filling in a tooth. It is common knowledge that dentists use a shim or matrix, usually made of a metal or plastic material, to limit the flow of filling material to adjacent teeth and the approximal space. A second object when making a filling is to separate the teeth by placing a small tension on the teeth by means of a wedge. The placing of a small tension on the teeth allows the teeth to return to the original position, in which the teeth are in direct contact with each other, after the filling is completed.

Placing of a matrix band and achieving a good contact point after excavation for fillings is often a time consuming and pain staking procedure. Matrices of the past have generally had flat barriers that are held against the tooth and gums by small wooden or plastic wedges. The small loose wedges are difficult to handle and causes discomfort and pain. Furthermore, since the matrices of the past tend to be relatively inflexible and not anatomically shaped, they do not adequately seal against the tooth. The sharp metal matrix, when placed in direct contact with the gums, also creates cuts and discomfort. Thus, the wedge and matrix combinations of the past lack the ability to provide an adequate seal with the tooth, avoiding damage to the gums and providing a comfortable treatment for the patient.

Alternatives such as sectional matrixes in combination with retention are also very cumbersome and time consuming to place correctly. The tension created on the teeth from the tightening of the metal matrix as well as the sharp metal matrix being placed in direct contact with the gums of the patient creates pain and increases the risk of causing gingivitis during a dental procedure.

SUMMARY

A dental instrument, suitable for use when creating a dental filling is provided. The dental instrument comprises a wedge and a matrix. The matrix is fixedly attached to the wedge, and the wedge is adapted to be inserted into the approximal space between two teeth of a patient. The wedge comprises a bow shape along a length axis of the wedge, the matrix comprises a first bow shape along a length axis of the matrix, and the matrix comprises a second bow shape along an axis perpendicular to the length axis of the matrix.

According to one embodiment the bow shape of the wedge comprises at least two curvatures along the length axis of the wedge.

According to one embodiment the wedge comprises a wing, which could be adapted to be collapsible and/or partly elastic.

According to one embodiment of the dental instrument, the matrix further comprises a bowl shaped area.

The dental instrument according to any of the embodiments above could be adapted to be disposable.

A disposable system suitable for use when creating a dental filling is further provided. The disposable system comprises a disposable protective member adapted for insertion in the approximal space between two teeth when excavating at least one of the teeth in connection with said approximal space. Furthermore the system comprises a dental instrument comprising a wedge and a matrix. The matrix is fixedly attached to the wedge and the wedge is adapted to be inserted into the approximal space between two teeth. The wedge comprises a bow shape along a length axis of the wedge, the matrix comprises a first bow shape along a length axis of the matrix, and the matrix comprises a second bow shape along an axis perpendicular to the length axis of the matrix.

A method of creating a filling in a tooth using the dental instrument according to any of embodiments above is further provided. The method comprises the steps of inserting the dental instrument according to any of the embodiments above in the approximal space between two teeth from the buccal or lingual side thereof, positioning a material, adapted to create a filling, in contact with the tooth and the dental instrument, hardening the material, and removing the dental instrument. According to one embodiment the dental instrument comprises at least one wing which could be collapsible and/or partly elastic.

BRIEF DESCRIPTION OF THE DRAWINGS

The embodiments are now described, by way of example, with reference to the accompanying drawings, in which.

DETAILED DESCRIPTION

Figure 1:
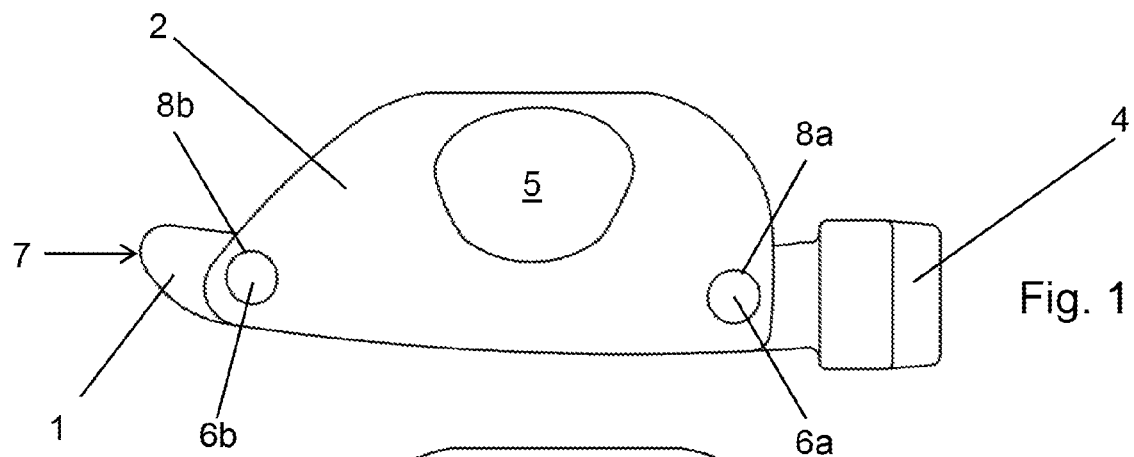
FIG. 1 shows the dental instrument from the side adapted to be in contact with the tooth receiving the filling.

Approximal space is to be understood as the space between two teeth.

Contact point is to be understood as the point on a tooth in which said tooth is in contact with another tooth.

Collapsible structure is to be understood as a structure adapted to collapse or deform when a certain amount of strain is placed thereon.

Partly elastic is to be understood as a materials ability to deform partly in an elastic way and partly in an inelastic way, i.e. after deformation of a partly elastic structure said structure only partly returns to its original shape or position.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

FIG. 1 shows a dental instrument adapted to be used in the creation of a filling to treat dental caries. The dental instrument is mainly adapted for use in restoring a tooth having a smooth surface destroyed by dental caries. In FIG. 1 the dental instrument is shown from the side adapted to be in contact with a dental filling. The dental instrument, according to this embodiment, comprises a wedge 1 having a tapering end 7 adapted to be inserted between two teeth from the buccal or mesial side thereof. The other end of said wedge 1 comprises a handling portion 4 adapted to facilitate the dentists handling of the dental instrument. According to the embodiment shown in FIG. 1 the wedge 1 and the handling portion 4 are portions of the same part, preferably made of a polymer material, such as polypropylene or polyethylene. The dental instrument further comprises a matrix 2 fixated to the wedge 1 by means of two fixating members 6a,b which provide a clamping effect arising from the top part of the fixating members 6a,b being slightly dilated after being placed in holes 8a,b of the matrix 1. The matrix 1 is further fixated by the adhesive effect that the polymer material presents when heated. However, according to other embodiments, said fixating members 6a,b can be assisted or replaced by an additional adhesive substance. According to this embodiment the matrix 2 is made of stainless steel, however, the matrix 2 being made of another metal or plastic material is also conceivable. The matrix 1 further comprises a bowl shaped area 5 having a concave surface directed towards the tooth receiving a filling; the bowl shaped area 5 is adapted to facilitate the creation of a contact point between the tooth receiving a filling and the adjacent tooth. Said contact point being an important feature blocking the approximal space and limiting the amount of food remains building up therein. Furthermore the bowl shaped area 5 eliminates the need for the dentist to burnish the matrix 2 to create a suitable shape of the filling.

Figure 2:
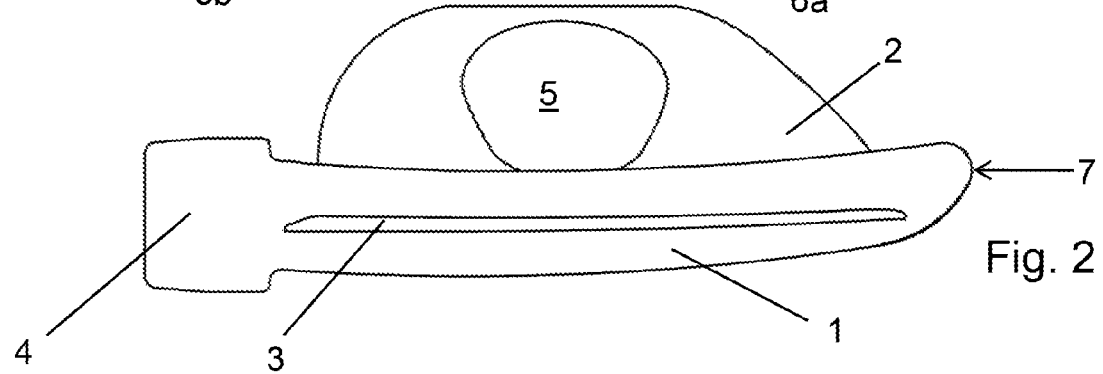
FIG. 2 shows the dental instrument from the side adapted to be in contact with a tooth adjacent to the tooth receiving the filling.

FIG. 2 shows the dental instrument of FIG. 1 from the side adapted to be in contact with the tooth adjacent to the tooth to receive a dental filling. The wedge 1 having a tapering end 7 and a handling portion 4. The wedge 1 further comprises a wing 3 extending along a length axis of the wedge 1. According to the embodiment shown in FIG. 2 the wing 3 is a portion of the same part as the wedge 1 and the handling member 4. The wing 3 is fixated to the wedge 1 along a length axis of said wedge 1 at a distance from the holding member 4 which enables the wing 3 to be collapsible in a partly elastic way when introduced between two teeth, see also FIG. 7. FIG. 2 furthermore shows the bowl shaped area 5 of the matrix 2 from the side adapted to be in contact with the tooth adjacent to the tooth to receive a dental filling.

Figures 3, 4:
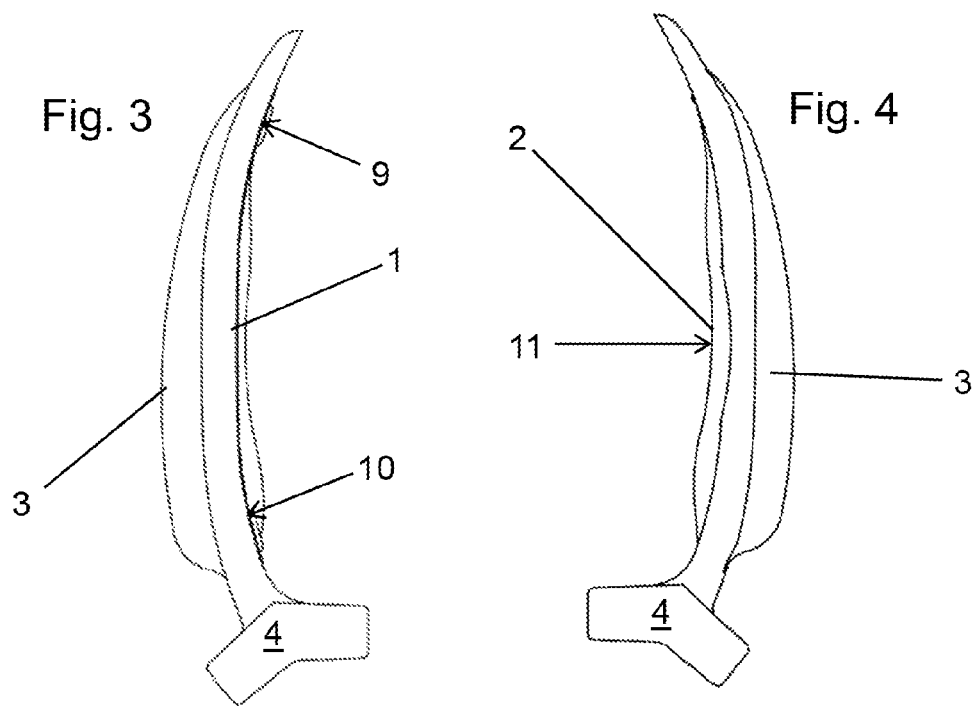
FIG. 3 shows the dental instrument from underneath, i.e. the side adapted to be in contact with the gums.
FIG. 4 shows the dental instrument from above.

FIG. 3 shows the dental instrument of FIGS. 1 and 2 from underneath. The wedge 1 comprises a bow shape having a first curvature 9 having a first radius, and a second curvature 10 having a second radius along a length axis X of said wedge 1. The surface comprising said first and second curvatures 9, 10 constitutes the contacting surface between the matrix 2 and the wedge 1 and enables the matrix 2 to present the corresponding surface, which provides a sealing between the tooth receiving the filling and the matrix 2. FIG. 3 furthermore shows the collapsible wing 3 from underneath.

FIG. 4 shows the dental instrument of FIGS. 1, 2 and 3 from above wherein the matrix 2 shows a first section comprising a first bow shape 11 along a length axis X of the wedge 1. The matrix 2 further comprises a bowl shaped area 5 that assists in the creation of a contact line between the tooth adapted to receive a filling and the adjacent tooth. FIG. 4 furthermore shows the collapsible wing 3 from above. The collapsible wing 3 and the bowl shaped area 5 are also shown in FIG. 7.

Figure 5:
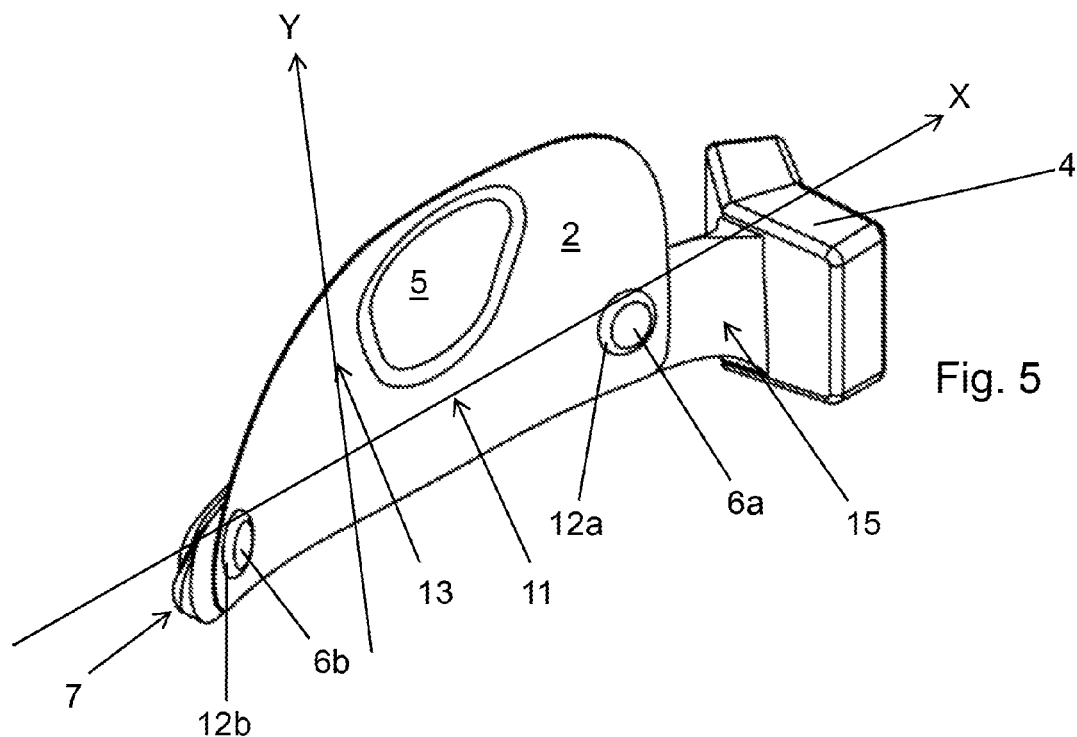
FIG. 5 shows the dental instrument from the side adapted to be in contact with the tooth receiving the filling, in a perspective view.

FIG. 5 shows the dental instrument of FIGS. 1, 2, 3 and 4 in a perspective view from the side in contact with the tooth receiving a filling. The matrix 2 fixated to the wedge 1 has a first bow shape 11 along a length axis X, said first bow shape 11 being adapted to create a tight seal between the matrix 2 and the tooth receiving the filling, from the buccal and lingual side thereof. The matrix 2 further comprises a second bow shape 13 along an axis Y perpendicular to the length axis X of the wedge 1, said second bow shape 13 being adapted to create a tight seal between the matrix 2 and the tooth receiving the filling on the proximal side thereof, thus preventing overhang of said filling. FIG. 5 furthermore shows the fixating members 6a,b being slightly dilated and hence creating a clamping portion 12a,b clamping the matrix 2 to the wedge 1. A contacting surface 15 of the wedge 1 to which the matrix 2 is fixated is also shown in FIG. 5.

Figure 6:
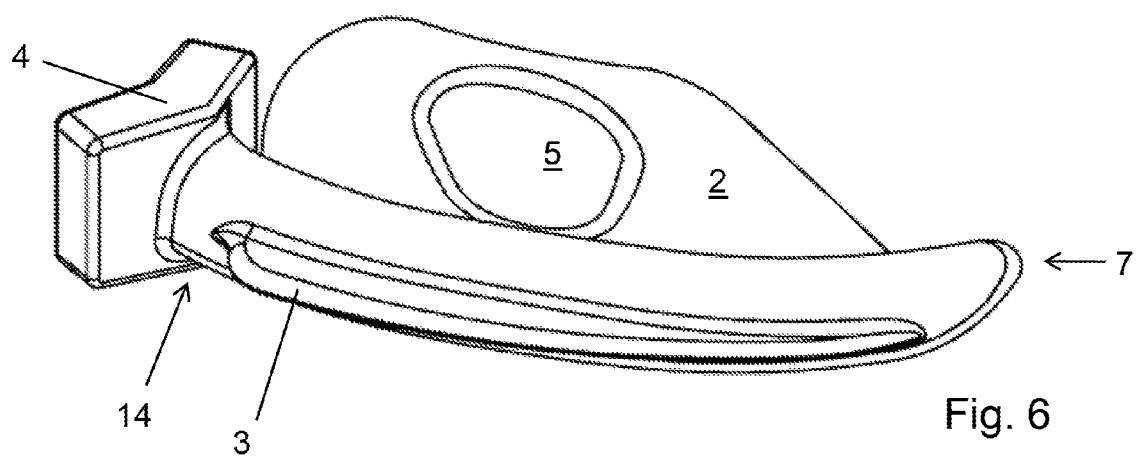
FIG. 6 shows the dental instrument from the side adapted to be in contact with the tooth adjacent to the tooth receiving the filling, in a perspective view.

FIG. 6 shows the dental instrument of FIGS. 1, 2, 3, 4 and 5 in a perspective view from the side adapted to be in contact with the tooth adjacent to the tooth adapted to receive a dental filling. In the view of FIG. 6 a distance 14 between the handling portion 4 and the collapsible wing 3 is shows. The distance between the handling portion 4 and the collapsible wing 3 enables the collapsible wing to be partly elastic and thereby push and rotate the wedge 1 which in turn pushes the matrix 2 against the tooth receiving the filling providing said sealing between the matrix 2 and tooth receiving the filling, also shown in FIG. 7.

Figure 7:
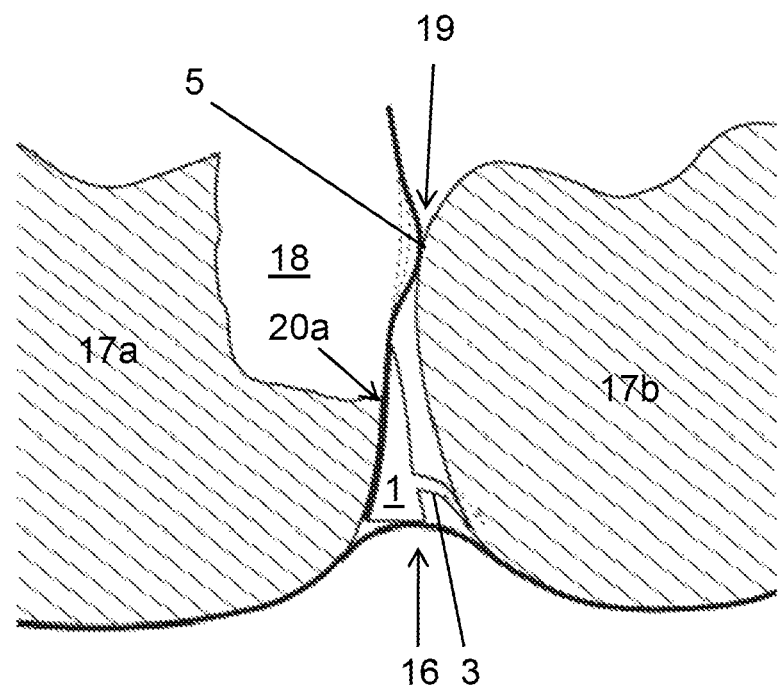
FIG. 7 shows a section of two teeth and the dental instrument placed in the approximal space there between, from the buccal side thereof.

FIG. 7 shows the approximal space 16 between a tooth receiving a filling 17a and an adjacent tooth 17b. A cavity 18 adapted to receive said filling has, for example, been created in said tooth 17a using a dental drill. The dental instrument has been inserted into the approximal space 16 from the buccal or lingual side of the teeth. The wedge 1 is positioned with the bottom part in connection with the gums and the wing 3 is partly collapsed and assists in sealing between the tooth receiving filling 17a and the matrix 2 through the wings 3 elastic properties pressing the wedge 1 and thus the matrix 2 against said tooth. As shown in FIG. 7, the bowl shaped area 5 of the matrix 2 assists in the creation of a contact point 19 between the tooth adapted to receive a filling 17a and the adjacent tooth 17b. A contacting line 20a in the base part of the filling is the area in which there is a risk of a damaging overhang being created. An overhang of excess material between the teeth creates a pocket in which food remains are assembled, which in many instances leads to renewed decay or gingivitis. Overhang created between the teeth is very cumbersome to remove after the filling has been hardened, since the dentists can not reach the area using a powered instrument and is therefore left with the use of abrasive strips. To avoid an overhang it is of utmost importance that a proper seal is created in the contact line 20a between the matrix 2 and the tooth receiving the filling 17a.

Figure 8:
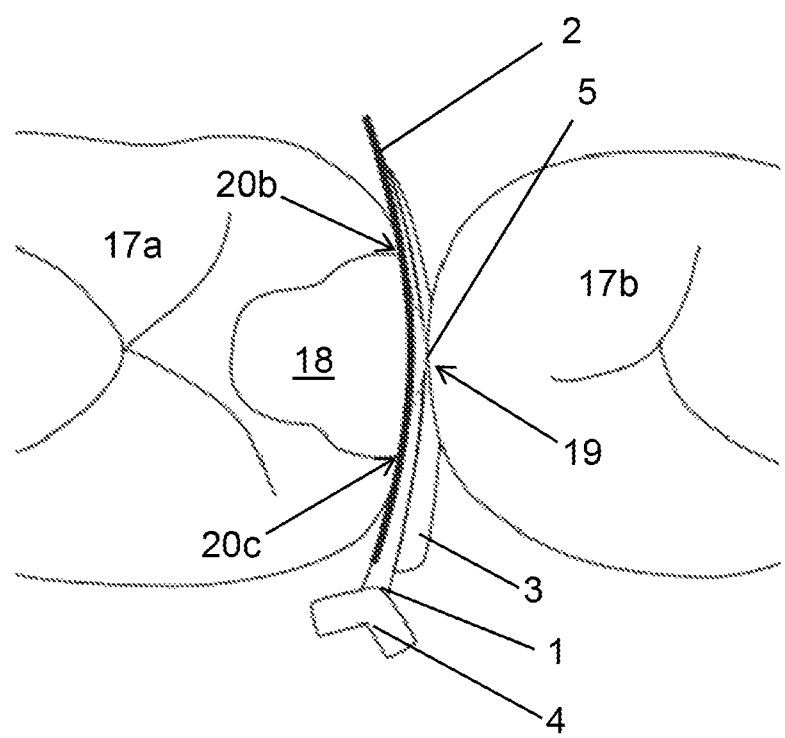
FIG. 8 shows two teeth and the dental instrument placed in the approximal space there between, from above.

FIG. 8 shows the dental instrument when said instrument is positioned between a tooth receiving a filling 17a and an adjacent tooth 17b from above. The dental instrument having its matrix 2 tightly fixated to the tooth receiving the filling through the matrix 2 having a bow shape 11 along a length axis X of the wedge 1. The matrix 2 thus making sure that the filling material does not penetrate the seal between the matrix 2 and the tooth receiving the filling 17a in the two contacting lines 20b,c on the buccal and lingual side of the tooth 17a. FIG. 8 also shows how the bowl shaped area 5 of the matrix 2 assist in the creation of a contact point 19 between said two teeth 17a,b and facilitate formation of a filling within desired boundaries. The placing of the dental instrument in the approximal space 16 from the buccal or mesial side of the teeth facilitate and speeds up the placing of the matrix 2 as well as lowering the probability of misplacement, which could result in improper sealing between the matrix 2 and the tooth receiving the filling.

Figure 9:
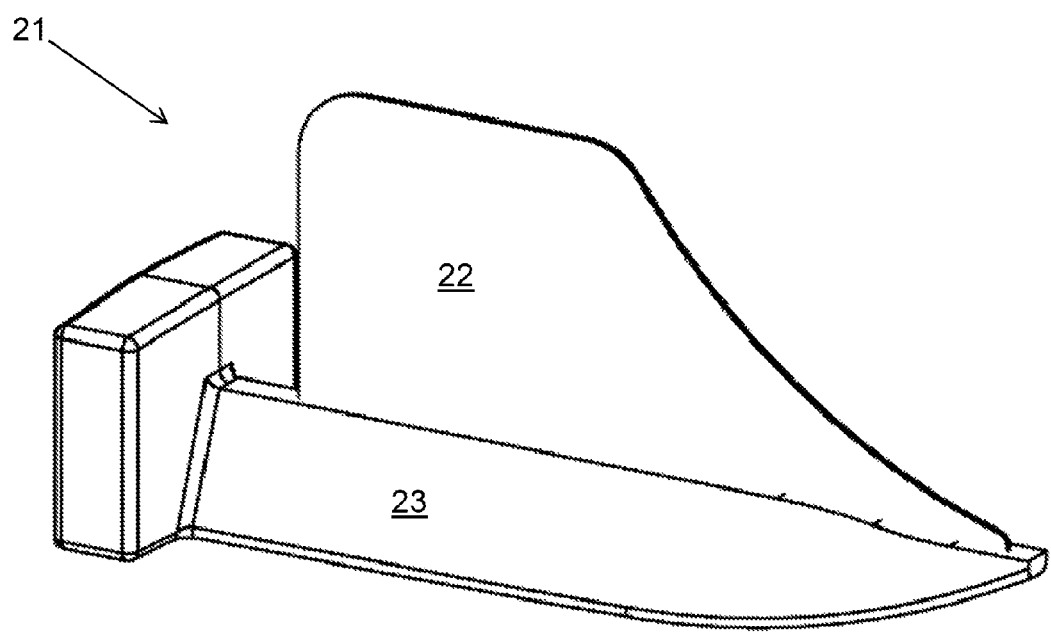
FIG. 9 shows a protective member in a perspective view.

FIG. 9 shows a disposable protective member 21 adapted for insertion in the approximal space 16 between two teeth 17a,b when excavating at least one of the teeth 17a,b in connection with the approximal space 16. The disposable protective member 21 comprises a metal shim 22 for protecting the tooth and a wedge member 23 for fixating the protective member 21 in the approximal space between two teeth.

The reference to any prior art in this specification is not, and should not be taken as, an acknowledgement or any suggestion that the referenced prior art forms part of the common general knowledge in Australia, or in any other country.

The invention is not restricted to the described embodiments in the figures, but may be varied freely within the scope of the claims.

The invention claimed is:

1. A dental instrument suitable for use when creating a dental filling, said instrument comprising a wedge and a matrix, wherein said matrix is fixedly attached to a first side of said wedge, and wherein said wedge is adapted to be inserted into an approximal space between two teeth, characterized in that:
    a. said wedge comprises a bow shape along a length axis of said wedge, wherein said bow shape extends along a surface adapted to be directed towards the tooth receiving the filling,
    b. said matrix comprises a first bow shape along a length axis of said matrix, and
    c. said matrix comprises a second bow shape along an axis perpendicular to said length axis of said matrix,
    wherein the bow shape of the wedge and the first bow shape of the matrix have a concave surface on the first side configured to form a seal between the matrix and the tooth receiving the filling; and wherein the wedge further comprises partly elastic collapsible wing affixed only to a second side of said wedge, opposite the concave surface.

2. The dental instrument according to claim 1, wherein said bow shape of said wedge comprises at least two curvatures along said length axis of said wedge.

3. The dental instrument according to claim 1, wherein said matrix further comprises a bowl shaped area having a third bow shape along a length axis of the bowl shaped area, and a fourth bow shape along an axis vertical to said length axis of the bowl shaped area, wherein said third bow shape has a smaller radius than said first bow shape, and said fourth bow shape has a smaller radius than said second bow shape.

4. The dental instrument according to claim 1, wherein said dental instrument is adapted to be disposable.

5. A disposable system suitable for use when creating a dental filling, said disposable system comprising:
    a. a disposable protective member adapted for insertion in an approximal space between two teeth, when excavating at least one of the teeth in connection with said approximal space, wherein said protective member comprises a shim for protecting the tooth, and a wedge member for fixating the protective member in the approximal space between two teeth, and
    b. a dental instrument comprising a wedge and a matrix, wherein said matrix is fixedly attached to a first side of said wedge, and wherein said wedge is adapted to be inserted into the approximal space between two teeth, characterized in that:
        i. said wedge comprises a bow shape along a length axis (X) of said wedge, wherein said bow shape extends along a surface adapted to be directed towards the tooth receiving the filling,
        ii. said matrix comprises a first bow shape along a length axis (X) of said matrix, and that
        iii. said matrix comprises a second bow shape along an axis (Y) perpendicular to said length axis of said matrix,
        wherein the bow shape of the wedge and the first bow shape of the matrix have a concave surface on the first side configured to form a seal between the matrix and the tooth receiving the filling; and wherein the wedge comprises a partly elastic collapsible wing affixed only to a second side of said wedge, opposite the concave surface.

6. A method of creating a filling in a tooth characterized in the steps of:
    a. providing a dental instrument comprising a wedge and a matrix, wherein said matrix is fixedly attached to a first side said wedge, and wherein said wedge is adapted to be inserted into an approximal space between two teeth, characterized in that said wedge comprises a bow shape along a length axis of said wedge, wherein said bow shape extends along a surface adapted to be directed towards the tooth receiving the filling, said matrix comprises a first bow shape along a length axis of said matrix, and that said matrix comprises a second bow shape along an axis perpendicular to said length axis of said matrix wherein the bow shape of the wedge and the first bow shape of the matrix have a concave surface on the first side configured to form a seal between the matrix and the tooth receiving the filling;
    b. inserting said dental instrument in the approximal space between two teeth from the buccal or lingual side thereof, such that required sealing between the matrix and the tooth is created,
    c. positioning a material, adapted to create said filling, in contact with said tooth and said dental instrument,
    d. hardening said material, and
    e. removing said dental instrument;
    wherein the wedge comprises a partly elastic collapsible wing affixed only to a second side of said wedge, opposite the concave surface.

* * * * *